United States Patent [19]

Casagrande et al.

[11] Patent Number: 5,138,084
[45] Date of Patent: Aug. 11, 1992

[54] PROCESS FOR THE PREPARATION OF 4-O-PHOSPHATES OF DOPAMINE AND DOPAMINE DERIVATIVES

[75] Inventors: Cesare Casagrande, Arese; Francesco Santangelo, Milan, both of Italy

[73] Assignee: SIMES Societa Italiana Medicinali e Sintetici S.p.A., Vicenza, Italy

[21] Appl. No.: 612,508

[22] Filed: Nov. 14, 1990

[30] Foreign Application Priority Data

Nov. 22, 1989 [IT] Italy .............................. 22486 A/89

[51] Int. Cl.$^5$ .............................................. C07F 9/37
[52] U.S. Cl. ..................................... 558/88; 558/106; 558/110; 558/177; 558/210

[58] Field of Search ............... 558/110, 210, 177, 106, 558/88

[56] References Cited

FOREIGN PATENT DOCUMENTS 0167204  1/1986  European Pat. Off. ............ 558/110

*Primary Examiner*—James H. Reamer
*Attorney, Agent, or Firm*—Stevens, Davis, Miller & Mosher

[57] ABSTRACT

A process for the preparation of 4-O-phosphates of dopamine and dopamine derivatives by treatment of a mixture of both 3-O-phosphate and 4-O-phosphate isomers with a strong mineral acid and optional esterification of the so obtained phosphoric ester of dopamine or dopamine derivatives is described.

7 Claims, No Drawings

PROCESS FOR THE PREPARATION OF 4-O-PHOSPHATES OF DOPAMINE AND DOPAMINE DERIVATIVES

The present invention relates to a process for the preparation of monophosphates and particularly it relates to a process for the preparation of 4-0-phosphates of dopamine and dopamine derivatives.

The European patent No. 0 167 204 (SIMES Societa Italiana Medicinali e Sintetici S.p.A.) describes a method for improving the absorption and the effectiveness of catecholamines consisting in the monophosphorylation of one of the catecholic hydroxyl groups.

However, the monophosphorylation processes therein described require the use of intermediates which are selectively protected on the catecholic function or a separation by chromatography or crystallization from mixtures containing both 3-O-phosphate and 4-O-phosphate.

We have now found that mixtures containing both 3-O-phosphate and 4-O-phosphate of dopamine or dopamine derivatives of formula

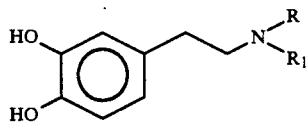

wherein
R is a hydrogen atom, a $C_1$-$C_6$ alkyl, a $C_1$-$C_6$ phenylalkyl optionally substituted by alkoxy groups, alkyl groups or halogen atoms, or an acyl of a natural aminoacid; and
$R_1$ is a hydrogen atom, a $C_1$-$C_6$ alkyl or a $C_1$-$C_6$ phenylalkyl optionally substituted by alkoxy groups, alkyl groups or halogen atoms;
are converted into the only 4-O-phosphate isomer which is readily isolated as the sole product from the reaction mixture in high yield and high purity, by treatment with a strong mineral acid.

Therefore, this invention relates to a process for the preparation of 4-O-phosphates of dopamine and dopamine derivatives comprising (i) the monophosphorylation of a compound of formula

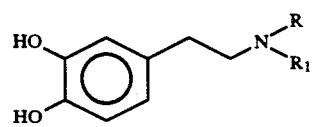

wherein
R is a hydrogen atom, a $C_1$-$C_6$ alkyl, a $C_1$-$C_6$ phenylalkyl optionally substituted by alkoxy groups, alkyl groups or halogen atoms, or an acyl of a natural aminoacid; and
$R_1$ is a hydrogen atom, a $C_1$-$C_6$ alkyl or a $C_1$-$C_6$ phenylalkyl optionally substituted by alkoxy groups, alkyl groups or halogen atoms;

(ii) the isomerization of the so obtained 3-O-phosphate and 4-O-phosphate mixture by treatment with a strong mineral acid to yield a compound of formula

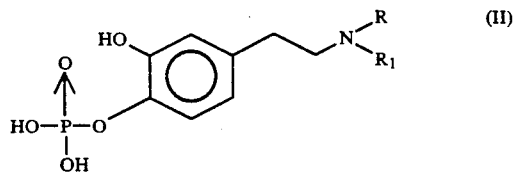

wherein R and $R_1$ have the above reported meanings; and (iii) the optional esterification of the compound of formula II to give a compound of formula

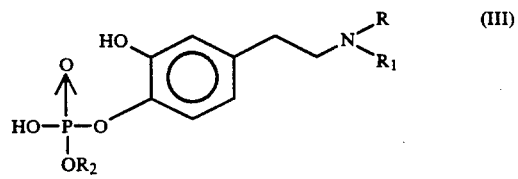

wherein
R and $R_1$ have the above mentioned meanings; and
$R_2$ is a phenylalkyl having 1 to 3 carbon atoms in the alkyl moiety or a $C_1$-$C_6$ alkyl optionally substituted by hydroxyl, alkoxy, acyloxy, amino, carboxy or alkoxycarbonyl groups.

The process of the present invention is shown in the following scheme.

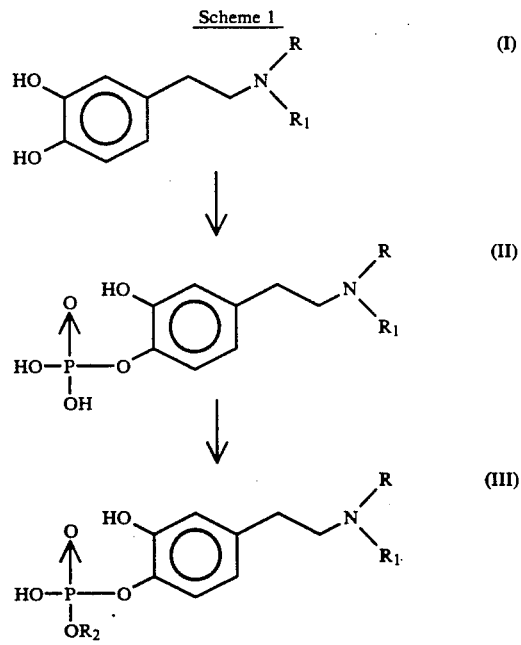

Scheme 1 wherein
R and $R_1$ have the above mentioned meanings; and
$R_2$ is a phenylalkyl having from 1 to 3 carbon atoms in the alkyl moiety or a $C_1$-$C_6$ alkyl optionally substituted by hydroxyl, alkoxy, acyloxy, amino, carboxy or alkoxycarbonyl groups.

The compounds of formula II and III are described in the above cited European Patent.

The dopamine derivative of formula I is monophosphorylated according to conventional methods with, for example, phosphorylating agents such as orthophosphoric acid, pyrophosphoric acid, phosphorus pentoxide, polyphosphoric acid, chlorophosphoric acid, phosphorus oxychloride and phosphorus oxybromide.

The mixture of 3-O-phosphate and 4-O-phosphate isomers is dissolved in a strong mineral acid and the 4-O-phosphate isomer of formula II separates by cooling as the only product.

Then, the so obtained compound of formula II is optionally esterified to achieve the phosphoric diesters of formula III.

Alternatively, the compounds of formula II or III, wherein one of R and $R_1$ is different from hydrogen, can be prepared from the corresponding compounds of formula II or III wherein at least one of R and $R_1$ is a hydrogen atom, by acylation or alkylation of the amino group.

The acylation reaction is carried out by treatment with suitably protected natural aminoacids and is then followed by the optional deprotection to give the compounds of formula II or III wherein R is an acyl of a natural aminoacid.

The alkylation can be carried out by reaction with alkyl or phenylalkyl halides or with esters of alkyl or arylsulfonic acids, or, alternatively, by condensation with aldehydes or ketones and subsequent reduction with hydrides or by hydrogenation.

The compounds of formula II or III wherein at least one of R or $R_1$ is a $C_1$-$C_6$ alkyl or a $C_1$-$C_6$ phenylalkyl optionally substituted by alkoxy groups, alkyl groups or halogen atoms are so obtained.

Specific examples of compounds which can be prepared according to the process of this invention are:
dopamine 4-O-dihydrogenphosphate
N-methyldopamine 4-O-ethylhydrogenphosphate
dopamine 4-O-dihydrogenphosphate hydrochloride
N-methyldopamine 4-O-dihydrogenphosphate
N-methyldopamine 4-O-dihydrogenphospate hydrochloride
N-(L-gamma-glutamyl)dopamine 4-O-dihydrogenphosphate
N-(L-gamma-glutamyl)dopamine 4-O-ethylhydrogenphosphate
bis[N-(L-gamma-glutamyl)dopamine 4-O-ethylhydrogenphosphate] calcium salt
N-(L-gamma-glutamyl)dopamine 4-O-(3-pivaloyloxypropyl)hydrogenphosphate
bis[N-(L-gamma-glutamyl)dopamine 4-O-(3-pivaloyloxypropyl)hydrogenphosphate]calcium salt
N,N-di-n.propyldopamine 4-O-dihydrogenphospate
dopamine 4-O-ethylhydrogenphospate
N-ethyldopamine 4-O-dihydrogenphospate
N-ethyldopamine 4-O-dihydrogenphosphate hydrochloride
dopamine 4-O-(3-pivaloyloxypropyl)hydrogenphosphate
N-glycyl-dopamine 4-O-dihydrogenphosphate The treatment of the mixture of phosphorylated products, obtained starting from the dopamine derivative of formula I, with a strong mineral acid results in the isomerization reaction shown in the following scheme

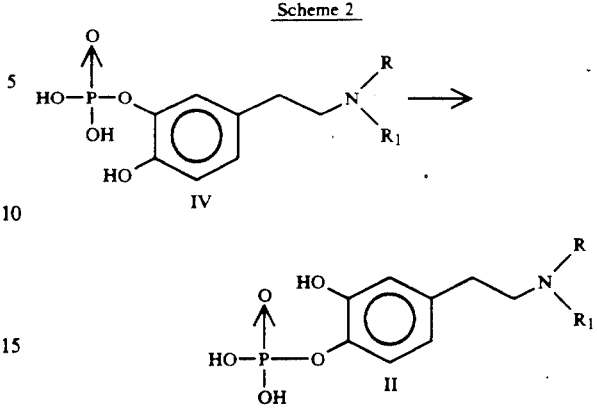

Scheme 2 wherein
R and $R_1$ have the above mentioned meanings;
and in the contemporaneous crystallization of the monophosphate of formula II in the form of the salt of said mineral acid.

The isomerization reaction, which is a further object of the present invention, is carried out by dissolving the mixture of both the 3-O-phosphate of formula IV and the 4-O-phosphate of formula II, in a strong mineral acid optionally in the presence of a solvent.

The reaction can also be carried out directly in the same phosphorylation reaction medium after decomposition, according to usual methods, of the excess of the phosphorylating agent, if any.

Examples of strong mineral acids are hydrochloric acid, hydrobromic acid and sulfuric acid.

Concentrate hydrochloric acid is preferably used.

Suitable solvents are lower alcohols such as, for example, methanol, ethers such as, for example, diethylene glycol, dimethyl ether, ethyl ether and dioxane, ketones such as, for example, acetone or mixtures of water and a watermiscible organic solvent.

The 4-O-phosphate of formula II separates from the reaction medium in the form of the salt of the used acid by mere cooling of the acid solution, generally at a temperature of from 0 to 10° C.

An important feature of this invention is that, the isomerization of compound IV is almost complete and results in the 4-O-phosphate isomer in a very high yield, irrespective of the ratio of 3-O-phosphate of formula IV to 4-O-phosphate of formula II in the starting mixture.

Furthermore, the unreacted dopamine derivative I still present in the phosphorylation mixture, if any, is concentrated in the crystallization liquors from which it can be easily recovered to be phosphorylated again.

As shown in Scheme 1, the 4-O-phosphate of formula II can be esterified to the phosphoric diesters of formula III.

This esterification reaction can be carried out according to several conventional methods.

However, we have found, and this is a further object of the present invention, that the esterification reaction may be advantageously carried out by treating a solution of a compound of formula II, with a compound of formula $$R_2X \qquad (V)$$

wherein
$R_2$ has the above mentioned meanings, and

X is a leaving group such as halogen, preferably iodine, or an alkyl or arylsulfonyloxy group, preferably a methylsulfonyloxy group, in a suitable aprotic organic solvent and in the presence of a tetraalkylammonium hydroxide.

This esterification reaction is preferably carried out by using tetramethylammonium hydroxide in an aprotic organic solvent selected from acetonitrile and toluene.

As far as we know this esterification reaction of monophosphate compounds has never been described for the selective preparation of 4-O-phosphate diesters of catecholamine-like compounds.

The selectivity of this esterification reaction for preparing 4-O-phosphate diesters of catecholamines is noticeable.

In fact, the phosphoric diester of formula III is obtained in high yields and, above all, selectively and highly pure.

Neither isomerization by-products nor phosphoric triesters are present in the esterification mixture.

This selectivity in the esterification reaction is even more surprising in view of the fact that significant amounts of by-products due to undesired isomerization were found when the reaction was carried out according to conventional methods, such as with alcohols in the presence of N,N-dicyclohexylcarbodiimide or after having activated the phosphate as chloride (by treatment, for example, with thionyl chloride).

Also when the esterification is carried out in the presence of bases different from tetraalkylammonium hydroxide, such as alkaline or alkaline-earth hydroxides, carbonates or bicarbonates, the phosphoric diesters III is obtained in low yields and mixed to several by-products which hinder purification.

It will be evident to the man skilled in the art that protection of the amino group of the compound of formula II can be convenient before carrying out the esterification reaction.

The protection reaction performed with protecting agents known in organic chemistry such as the halides of carbonic acid derivatives.

Preferred protecting groups are benzyloxycarbonyl and t.butoxycarbonyl.

At the end of the esterification reaction the protecting group, if any, is removed according to conventional techniques such as, for example, catalytic hydrogenation, to yield the compound of formula III.

Alternatively, as already mentioned, the compounds of formula II and III wherein one of R and $R_1$ is different from hydrogen can be prepared from the corresponding compounds of formula II or III wherein at least one of R and $R_1$ is a hydrogen atom.

Also in this case it can be convenient to make use of suitable protecting groups according to conventional techniques.

In order to better illustrate the present invention without limiting it, the following examples are now given.

EXAMPLE 1

Preparation of N-methyldopamine 4-0-dihydrogenphosphate hydrochloride

Method A

Into a ten-liter flask containing phosphorus pentoxide (781.5 g; 5.5. moles), 85% phosphoric acid (392.8 ml; 5.775 moles; d=1.695) was added dropwise, under vigorous stirring and nitrogen flow, keeping the temperature at about 150° C.

At the end of the addition, the suspension was kept at 150° C. up to complete dissolution.

The so obtained thick clear solution was cooled to 40° C. and then N-methyldopamine hydrochloride (800 g; 3.931 moles) was added.

The mixture was heated to 150° C. in 30 minutes, cooled to 60° C. and quickly diluted with water (2.4 l).

After further 30 minutes at 80° C., the solution was further diluted with water up to a finale volume of 12 l.

HPLC analysis [anionic exchange column, Spherisorb SAX 5 micron (Phase separation), mobile phase 0.02 M $NH_4H_2PO_4$] showed that the mixture contained N-methyldopamine (11%), N-methyldopamine 3-0-dihydrogenphosphate (29%) and N-methyldopamine 4-0-dihydrogenphosphate (31%).

The solution was applied on a strongly acid exchange resin Dowex M 15 column.

After washing of the column with water (16 l), the product was eluted with 1N HCl (50 l) which was collected and concentrated to small volume.

The residue was taken up with absolute ethanol (2 l) obtaining a first precipitation of compound (478 g).

The mother liquors were evaporated and the residue was taken up with ethanol (0.5 l) obtaining a further precipitation (110 g); by repeating the procedure a third crop of compound (30.5 g) was obtained. The three precipitates were combined obtaining a total amount of 618.5 g (55.5% yield) of N-methyldopamine 4-0-dihydrogenphosphate hydrochloride.

Method B

The phosphorylation reaction was repeated according to the procedure described for method A starting from 80 g (0.393 moles) of N-methyldopamine hydrochloride.

The reaction mixture was directly diluted with concentrated HCl (400 ml), keeping under stirring for 4 hours, and it was cooled at 5°–10° C. for 48 hours.

The precipitate was filtered, suspended in acetone under stirring, filtered again and dried under vacuum obtaining N-methyldopamine 4-O-dihydrogenphosphate hydrochloride (56.3 g; 50% yield).

The phosphorylation reaction was repeated according to the procedure described for method A starting from N-methyldopamine as free base, obtaining N-methyldopamine 4-0-dihydrogenphosphate hydrochloride substantially with the same yields.

EXAMPLE 2

Preparation of N-methyldopamine 4-0-dihydrogenphosphate

Into a flask containing water (2.7 l) under nitrogen flow, a 40% sodium hydroxide solution (420 ml) and N-methyldopamine 4-0-dihydrogenphosphate hydrochloride (1.196 kg; 4.216 moles), prepared as described in example 1, were added contemporaneously while the temperature was kept at from 15 to 20° C. and the pH of the suspension at from 3 to 5.

At the end of the addition (final pH about 4) and after vigorous stirring for further 30 minutes, the suspension was filtered.

The solid was washed with water, with ethanol and dried under vacuum obtaining N-methyldopamine 4-O-dihydrogenphosphate (1.005 kg; 96% yield).

m.p. 207°–209° C.

$^1$H-NMR (300 MHz, D$_2$O): delta (ppm): 2.75 (3H, s); 3.00 (2H, t); 3.47 (2H, t); 6.88 (1H, dd); 6.95 (1H, d); 7.29 (1H, d).

EXAMPLE 3

Preparation of dopamine 4-O-dihydrogenphosphate hydrochloride

A mixture of dopamine 3-O-dihydrogenphosphate and dopamine 4-O-dihydrogenphosphate in ratio 1:1 (123.6 g; 0.530 moles) was dissolved in concentrate HCl (300 ml) and cooled at 5°-10° C. for 48 hours.

The precipitate was filtered, suspended in acetone, kept under stirring for 30 minutes, filtered again and dried under vacuum.

Dopamine 4-O-dihydrogenphosphate hydrochloride (56 g) was obtained.

Further product (36 g) was obtained by evaporation to dryness of acetone and mother liquors, dissolution of the obtained residue in concentrate HCl (200 ml), cooling the thus obtained solution and filtration of the solid which separates by cooling.

As a total amount, 92 g of dopamine 4-O-dihydrogenphosphate hydrochloride (64% yield) was obtained, m.p. 147°-150° C. $^1$H-NMR (300 MHz, D$_2$O): delta (ppm): 2.90 (2H,t); 3.25 (2H, t); 6.63 (1H, dd); 6.90 (1H, d); 7.22 (1H, dd).

By working in a similar way the following compounds were obtained.

N-ethyldopamine 4-O-dihydrogenphosphate hydrochloride m.p. 150° C. (dec.).

$^1$H-NMR (300 MHz, D$_2$O): delta (ppm): 1.27 (3H, t); 2.94 (2H, t); 3.08 (2H, q); 3.28 (2H, t); 6.82 (1H, dd); 6.90 (1H, d); 7.23 (1H, dd).

N,N-di-n-propyldopamine 4-O-dihydrogenphosphate hydrochloride m.p. 181°-186° C. (inner salt).

$^1$H-NMR (300 MHz, D$_2$): delta (ppm): 0.97 (6H, t); 1.65-1.78 (4H, m); 2.99 (2H, t); 3.11-3.16 (4H, m); 3.48 (2H, m); 6.83 (1H, dd); 6.90 (1H, d).

EXAMPLE 4

Preparation of N-benzyloxycarbonyldopamine 4-O-dihydrogenphosphate

To a mixture of dopamine 4-O-dihydrogenphosphate hydrochloride (80 g; 0.295 moles), prepared as described in example 3, in 2N NaOH (594 ml; 1.188 moles), a 50% solution of benzyl chlorocarbonate in toluene (0.297 moles) and a 2N solution of NaOH (163 ml; 0.327 moles) were added dropwise contemporaneously at a temperature of from 5° to 10° C.

After 3 hours at 5° C., the reaction mixture was acidified up to pH 1.5 with 3N HCl.

The precipitate was filtered, taken up with ethyl ether, triturated and filtered again.

N-benzyloxycarbonyldopamine 4-O-dihydrogenphosphate sodium salt was obtained (97 g; 84% yield, m.p. 189°-191° C.) and suspended in ethyl acetate (900 ml).

0.3N HCl (829 ml) was added to the suspension.

The mixture was kept under stirring till complete dissolution and the organic phase was then separated.

The aqueous phase was again extracted twice with ethyl acetate.

The combined extracts were evaporated to dryness under vacuum at a temperature lower than 30° C.

The residue was taken up with methylene chloride obtaining N-benzyloxycarbonyldopamine 4-O-dihydrogenphosphate (79 g; 86% yield; m.p. 132°-134° C.).

$^1$H-NMR (300 Mhz, D$_2$O): delta (ppm): 2.70 (2H, t); 3.36 (2H, t); 5.05 (2H, s); 6.73 (1H, dd); 6.83 (1H, d); 7.16 (1H, dd); 7.30-7.48 (5H, m).

EXAMPLE 5

Preparation of N-benzyloxycarbonyldopamine 4-O-ethylhydrogenphosphate ammonium salt To a suspension of N-benzyloxycarbonyldopamine 4-O-dihydrogenphosphate (40 g; 0.1009 moles), prepared as described in example 4, in ethanol (400 ml), a 20% solution of tetramethylammonium hydroxide in methanol (0.218 moles) was added.

After complete dissolution, the solution was evaporated to dryness, the residue was taken up with acetonitrile (800 ml) and ethyl iodide (34 g; 0.218 moles) was added.

After three hours, the precipitate was filtered and the solution was evaporated to dryness under vacuum.

The obtained residue was taken up with 0.1N HCl (1.09 l) and extracted with ethyl acetate.

The organic phase was washed with a NaCl saturate solution (150 ml), basified with ammonia (10 ml) and evaporated to dryness.

The residue was taken up with methylene chloride and N-benzyloxycarbonyldopamine 4-O-ethylhydrogenphosphare ammonium salt (42 g; 93% yield) was obtained, as a pure oil by thin layer chromatography (eluent CH$_3$COH:H$_2$O:toluene:acetone:n-.butanol=1:1:1:1:1, detection I$_2$ vapours).

$^1$H-NMR (300 MHz, D$_2$O): delta (ppm): 1.25 (3H, t); 2.72 (2H, t); 3.37 (2H, t); 4.03 (2H, q); 5.06 (2H, s); 6.76 (1H, dd); 6.85 (1H, d); 7.18 (1H, dd); 7.32-7.49 (5H, m).

By working in a similar way, the following compound was obtained:

N-benzyloxycarbonyldopamine 4-O-(3-pivaloyloxypropyl)hydrogenphosphate ammonium salt $^1$H-NMR (300 MHz, D$_2$O): delta (ppm): 1.00 (9H, s); 1.83 (2H, quintet); 2.61 (2H, t); 3.26 (2H, t); 3.93-4.02 (4H, m); 4.93 (2H, s); 6.58 (1H, dd); 6.78 (1H, d); 7.10 (2H, d); 7.15-7.25 (5H, m).

EXAMPLE 6

Preparation of dopamine 4-O-ethylhydrogenphosphate

A mixture of N-benzyloxycarbonyl dopamine 4-O-ethylhydrogenphosphate ammonium salt (42 g; 0.101 moles), prepared as described in example 5, and 10% palladium on activated charcoal (10 g) in 95% ethanol (800 ml) was hydrogenated.

At the end of hydrogen absorption, the catalyst was filtered and the solution was concentrated to a volume of about 80 ml.

Dopamine 4-0-ethylhydrogenphosphate (16.7 g; 63% yield) separated.

m.p. 180°-182° C. $^1$H-NMR (300 MHz, D$_2$): delta (ppm): 1.28 (3H, t); 2.95 (2H, t); 3.28 (2H, t); 4.08 (2H, q); 6.84 (1H, dd); 6.93 (1H, d); 7.25 (1H, dd).

By working in a similar way, the following compound was obtained:

Dopamine
4-O-(3-pivoloyloxypropyl)hydrogenphosphate
m.p. 203°-205° C.

¹H-NMR (300 MHz, D₂O): delta (ppm): 1.12 (9H, s); 1.99 (2H, q); 2.93 (2H, t); 3.27 (2H, t); 4.05–4.12 (4H, m); 6.82 (2H, dd); 6.90 (2H, d); 7.23 (2H, d).

EXAMPLE 7

Preparation of N-(L-gamma-glutamyldopamine) 4-O-dihydrogenphosphate

To a suspension of dopamine 4-O-dihydrogenphosphate hydrochloride (161 g; 0.6 moles), prepared as described in example 3, and sodium bicarbonate (151.6 g; 1.8 moles) in water (2 l), N-benzyloxycarbonyl-L-glutamic acid alpha-benzyl-gamma-(N-succinimido)diester (309 g; 0.66 moles) and absolute ethanol (1 l) were added.

The reaction mixture was warmed to 50°-55° C. and the dissolution was complete after an hour.

After further two hours a part of the solvent (about 1 l) was evaporated and the solution was then washed with ethyl acetate, acidified with concentrate HCl and extracted with ethyl acetate.

The combined organic extracts were washed with a 15% NaCl aqueous solution (3×400 ml), dried on sodium sulfate, filtered, basified with ammonia, diluted with ethanol and, at last, evaporated to dryness.

A residue (N-benzyloxycarbonyl-L-glutamyl-gamma-benzyl ester dopamine 4-O-dihydrogenphosphate ammonium salt) was obtained and used in the next step without further purification.

The crude was dissolved in water (1.5 l), diluted with ethanol (1.5 l) and 10% palladium on activated charcoal (72 g; 50% H₂O) was then added.

The suspension was hydrogenated under an initial pressure of 20-25 atmospheres and at a temperature of 25°-30° C.

After 5 hours, at the end of hydrogen absorption, the catalyst was filtered and the solution was evaporated to a volume of 600 ml.

The so obtained solution was acidified with concentrate HCl (75 ml), charcoal was added and the suspension was filtered washing with water up to a total volume of 850 ml.

The solution was further diluted with absolute ethanol (1.8 l) and seeded with some crystals of product (0.5 g).

The compound precipitated very quickly and after 2 hours it was filtered, washed first with 70% ethanol (250 ml) and then with ethanol (500 ml).

After drying at 50° C. under vacuum overnight, N-(L-gamma-glutamyl-dopamine) 4-O-dihydrogenphosphate (105 g; 58% yield) was obtained.

¹H-NMR (300 MHz, D₂O): delta (ppm): 2.08 (2H, q); 2.39 (2H, t); 2.76 (2H, t); 3.39-3.57 (2H, m); 4.79 (1H, t), 6.78 (1H, dd); 6.85 (1H, d); 7.18 (1H, dd).

By working in a similar way, the following compounds were obtained:

bis[N-L-gamma-glutamyldopamine) 4-O-ethylhydrogenphosphate]calcium salt

¹H-NMR (300 MHz, D₂O): delta (ppm): 1.28 (3H, t); 2.01-2.08 (2H, m); 2.32-2.38 (2H, m); 3.76 (2H, t); 3.45 (2H, t); 3.68 (1H, t); 4.06 (2H, q); 6.79 (1H, dd); 6.87 (1H, d); 7.20 (1H, dd).

bis[N-(L-gamma-glutamyldopamine) 4-O-(3-pivaloyloxypropyl)-hydrogenphosphate] calcium salt ¹H-NMR (300 Mhz, D₂O): delta (ppm): 1.13 (9H, s); 1.95-2.18 (4H, m); 2.32-2.38 (2H, m); 2.76 (2H, t); 3.45 (2H, t); 3.67-3.72 (H2H, m); 4.04-4.15 (4H, m); 6.78 (1H, dd); 6.86 (1H, d); 7.18 (1H, d).

N-glycyl-dopamine 4-O-dihydrogenphosphate
¹H-NMR (300 MHz, D₂O): delta (ppm): 2.76 (2H, t); 3.48 (2H, t); 3.70 (2H, s); 6.78 (1H, dd); 6.84 (1H, d); 7.17 (1H, dd).

We claim:

1. An improvement in a process for the preparation of 4-O-phosphates of dopamine and dopamine derivatives comprising (i) the monophosphorylation of a compound of formula

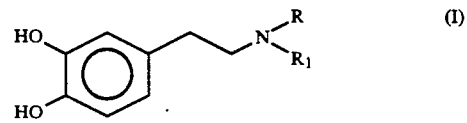

wherein

R is a hydrogen atom, a C₁-C₆ alkyl, a C₁-C₆ phenylalkyl optionally substituted by alkoxy groups, alkyl groups or halogen atoms, or an acyl of a natural aminoacid; and R₁ is a hydrogen atom, a C₁-C₆ alkyl or a C₁-C₆ phenylalkyl optionally substituted by alkoxy groups, alkyl groups or halogen atoms; and (ii) the optional esterification of a monophosphorylated compound to give a compound of formula

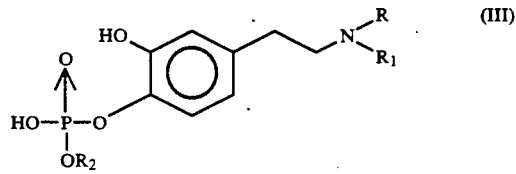

wherein

R and R₁ have the above-mentioned meanings; and

R₂ is a phenylalkyl having 1 to 3 carbon atoms in the alkyl moiety or a C₁-C₆ alkyl optionally substituted by hydroxyl, alkoxy, acyloxy, amino, carboxy or alkoxycarbonyl groups the improvement comprising the isomerization of the mixture of 3-O-phosphate and 4-O-phosphate obtained in step (i) before performing step (ii), said isomerization being performed by treating with a strong mineral acid to yield a compound of formula

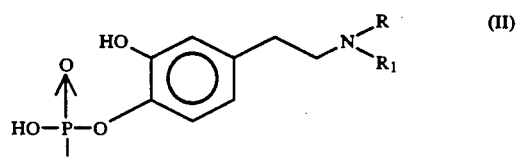

wherein

R and $R_1$ have the above-reported meanings.

2. A process according to claim 1, wherein the isomerization step is performed with a strong mineral acid selected from hydrochloric acid, hydrobromic acid and sulfuric acid optionally in the presence of a solvent.

3. An improvement in a process for the preparation of monophosphorylated dopamine and dopamine derivatives comprising
   (i) the monophosphorylation of a compound of formula

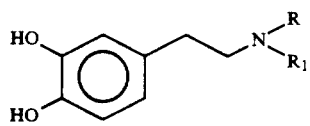

(I)

wherein
   R is a hydrogen atom, a $C_1$-$C_6$ alkyl, a $C_1$-$C_6$ phenylalkyl optionally substituted by alkoxy groups, alkyl groups or halogen atoms, or an acyl of a natural aminoacid; and
   $R_1$ is a hydrogen atom, a $C_1$-$C_6$ alkyl or a $C_1$-$C_6$ phenylalkyl optionally substituted by alkoxy groups, alkyl groups or halogen atoms; and
   (ii) the optional esterification of a monophosphorylated compound to give a compound of formula

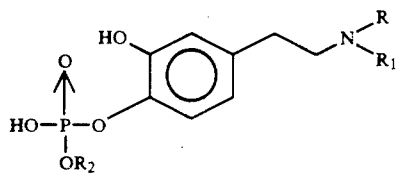

(III)

wherein
   R and $R_1$ have the above-mentioned meanings; and
   $R_2$ is a phenylalkyl having 1 to 3 carbon atoms in the alkyl moiety or a $C_1$-$C_6$ alkyl optionally substituted by hydroxyl, alkoxy, acyloxy, amino, carboxy or alkoxy-carbonyl groups
the improvement comprising carrying out the esterification step by treating a solution of a monophosphorylated compound with a compound of formula $R_2X$ (V)

wherein
   $R_2$ has the meanings mentioned in claim 1; and
   X is a leaving group selected from halogen, alkyl- and arylsulfonyloxy;
in a suitable aprotic organic solvent and in the presence of a tetraalkylammonium hydroxide,.

4. A process according to claim 3 wherein the tetraalkylammonium hydroxide is tetramethylammonium hydroxide.

5. An improvement in a process for the preparation of 4-O-phosphates of dopamine and dopamine derivatives comprising
   (i) the monophosphorylation of a compound of formula

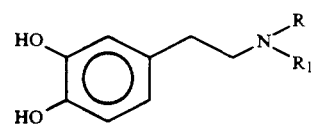

(I)

wherein
   R is a hydrogen atom, a $C_1$-$C_6$ alkyl, a $C_1$-$C_6$ phenylalkyl optionally substituted by alkoxy groups, alkyl groups or halogen atoms, or an acyl of a natural aminoacid; and
   $R_1$ is a hydrogen atom, a $C_1$-$C_6$ alkyl or a $C_1$-$C_6$ phenylalkyl optionally substituted by alkoxy groups, alkyl groups or halogen atoms; and
   (ii) the optional esterification of a monophosphorylated compound to give a compound of formula

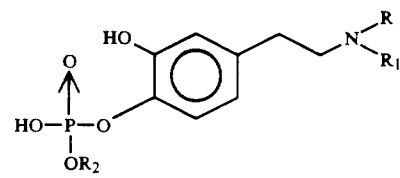

(III)

wherein
   R and $R_1$ have the above-mentioned meanings; and
   $R_2$ is a phenylalkyl having 1 to 3 carbon atoms in the alkyl moiety or a $C_1$-$C_6$ alkyl optionally substituted by hydroxyl, alkoxy, aryloxy, amino, carboxy or alkoxycarbonyl groups,
the improvement comprising
(a) the isomerization of the mixture of 3-O-phosphate and 4-O-phosphate obtained in step (i) before performing step (ii), said isomerization being performed by treatment with a strong mineral acid to yield a compound of formula

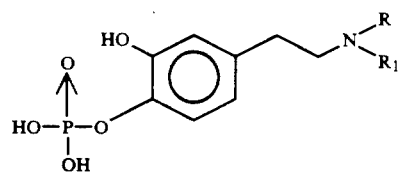

(II)

wherein
   R and $R_1$ have the above-reported meanings; and
(b) carrying out the esterification step by treating a solution of a compound of formula II with a compound of formula $R_2X$ (V)

wherein
   $R_2$ has the meanings mentioned in claim 1, and
   X is a leaving group selected from halogen, alkyl- and arylsulfonyloxy;
in a suitable aprotic organic solvent and in the presence of a tetraalkylammonium hydroxide.

6. A process according to claim 5, wherein step (a) is performed with a strong mineral acid selected from hydrochloric acid, hydrobromic acid and sulfuric acid optionally in the presence of a solvent.

7. A process according to claim 5 wherein the tetraalkylammonium hydroxide is tetramethylammonium hydroxide.

* * * * *